United States Patent [19]

Chang et al.

[11] Patent Number: 4,986,639
[45] Date of Patent: Jan. 22, 1991

[54] EYE PROTECTION DEVICE AGAINST BROADBAND HIGH INTENSITY LIGHT

[75] Inventors: David B. Chang, Tustin; Brian M. Pierce, Moreno Valley, both of Calif.

[73] Assignee: Hughes Aircraft Company, Los Angeles, Calif.

[21] Appl. No.: 296,643

[22] Filed: Jan. 13, 1989

[51] Int. Cl.⁵ .......................... G02B 5/23; G02F 1/01; G02F 1/07
[52] U.S. Cl. .................................... 350/354; 350/355; 350/356
[58] Field of Search .................. 350/354, 356, 355

[56] References Cited

U.S. PATENT DOCUMENTS 3,524,064 8/1970 Keyes .............................. 350/356 X
3,902,061 8/1975 Harris ............................. 350/354 X

OTHER PUBLICATIONS

"PLZT Electrooptic Shutter: Applications," J. Thomas Cutchen et al., Applied Optics, vol. 14, No. 8, Aug. 1975.
"Semiconductor Optical Shutter," R. H. Vought, R. L. Thompson, General Electric Company, Dec. 1966, Contract AF41(609)-2899, Project Task No. 630103.
"Recent Improvements in the Optical and Electrooptic Properties of PLZT Ceramics," G. H. Haertling and C. E. Land, Ferroelectrics, 1972, vol. 3, pp. 269–280, IEEE Trans. Sonics & Ultrasonics, SU-19, pp. 269–280.

Primary Examiner—Eugene R. LaRoche
Assistant Examiner—Michael Shingleton
Attorney, Agent, or Firm—Michael W. Sales; Wanda Denson-Low

[57] ABSTRACT

An eye protection device against broadband high intensity light sources, including a fast response component (picosecond to microsecond) and a slow response component (microsecond and longer). The fast response component consists of two thin semiconductor layers "sandwiched" between two transparent electrodes. The natures and dimensions of the semiconductor layers and the voltage bias applied to them are determined such that enough photo-excited electrons are generated in the first small bandgap layer so that the second large bandgap layer undergoes a rapid insulator-to-metal transition at the light-intensity threshold for eye damage. Upon becoming metal-like, this layer blocks the incident light. Below the damage threshold, the fast response component is transparent. The slow response component includes a PLZT (lanthanum-modified lead zirconium titanate) or similar electro-optic shutter. This component is transparent below the damage threshold. Finally, ballistic and chemical protection are obtained by embedding these slow and fast response components in a suitable plastic goggle.

22 Claims, 2 Drawing Sheets

EYE PROTECTION DEVICE AGAINST BROADBAND HIGH INTENSITY LIGHT

BACKGROUND OF THE INVENTION

The present invention relates to eye protection devices for preventing eye injuries due to incident broadband, high intensity light, and more particularly to such a device which is normally transparent, yet which becomes opaque within a few nanoseconds when irradiated by high intensity light over a broad band of wavelengths.

Military applications of single wavelength and tunable wavelength lasers operating in the visible (400–700 nm) and near-infrared (700–1200 nm) spectral regions are increasing rapidly. Consequently, the protection of the eyesight of military personnel against high intensity laser light from hostile and friendly forces is a major concern. A desirable protective device would be a goggle with the following major features. First, the goggle should be transparent over a broad wavelength range, unless irradiated at a light intensity above the threshold for eye damage. Second, the goggle should block the incident light a few nanoseconds after being irradiated above the damage threshold. Third, the goggle should provide ballistic and chemical protection.

At present, there is no eye protection device against high intensity light sources which (1) is transparent over a broad wavelength range, unless irradiated at a light intensity above the threshold for eye damage, and (2) becomes opaque within a few nanoseconds for intensities exceeding the threshold intensity for a broad band of wavelengths.

Devices have been developed to protect against high intensity light like a nuclear flash. However, none of these device are both (1) transparent over a broad wavelength range below the eye damage threshold, and (20 become opaque within a few nanoseconds for intensities exceeding the threshold for a broadband of wavelengths. A table of developed or potential devices, their response times, and their capability to offer broadband protection is given below.

| Device | Approximate Response Time (sec) | Broadband | Development Stage |
|---|---|---|---|
| Liquid crystal light value | $\sim 10^{-3}$ | Yes | Developed. |
| PLZT or other ferro-electric electro-optic shutter | $>10^{-6}$ | Yes | Developed. |
| Image converter | $>10^{-6}$ | Yes | Developed. Awkward for a foot soldier. |
| Holographic Diffraction Optics | $10^{-12}$–$10^9$ | No | Developed. |
| Photochromic | $>10^{-8}$ | Yes | Potential. Difficult to simultaneously transmit and protect against visible light. |
| Electrochromic Effect | $>10^{-9}$ | Yes | Potential. High fields ($10^6$–$10^7$) required. |
| Semiconductor Metal $VO_2$ Light Valve | $>10^{-9}$ | Yes (IR & Near IR) (Visible) | Potential. |
| Non-Linear Optical Phenomena | $>10^{-12} > 10^{-9}$ | Yes | Potential. Requires much higher light intensities than the damage threshold, or an awkward focussing assembly. |

In summary, the developed broadband devices do not have fast enough response times. The proposed devices may be capable of fast response times, but have the indicated problems regarding their development.

It is therefore an object of the invention to provide an eye protection device which is transparent over a broad wavelength range until irradiated at a light intensity above the threshold for eye damage, and which becomes opaque within a few nanoseconds for incident light intensities exceeding the threshold intensity for a broad band of wavelengths.

SUMMARY OF THE INVENTION

An eye protection device against broadband high intensity light sources is disclosed. The device comprises a fast response component (picosecond to microsecond) and a slow response component (microsecond and longer). The fast response component comprises two thin semiconductor layers "sandwiched" between two transparent electrodes and means for applying an electrical potential difference between the electrodes. The nature and dimensions of the semiconductor layers and the voltage bias applied to them are determined such that enough photo-excited electrons are generated in the first layer so that the second layer undergoes a rapid insulator-to-metal transition at the light-intensity threshold for eye damage. Upon becoming metal-like, this layer blocks the incident light. Below the damage threshold, the fast response component is transparent.

The slow response component consists of a PLZT (lanthanum-modified lead zirconate titanate) or similar electro-optic shutter. This component is transparent below the damage threshold.

The fast and slow response components may be embedded in a suitable plastic goggle in order to provide ballistic and chemical protection.

BRIEF DESCRIPTION OF THE DRAWINGS

These and other features and advantages of the present invention will become more apparent from the following detailed description of an exemplary embodiment thereof, as illustrated in the accompanying drawings, in which.

DETAILED DESCRIPTION OF THE PREFERRED EMBODIMENTS

Figure 1:
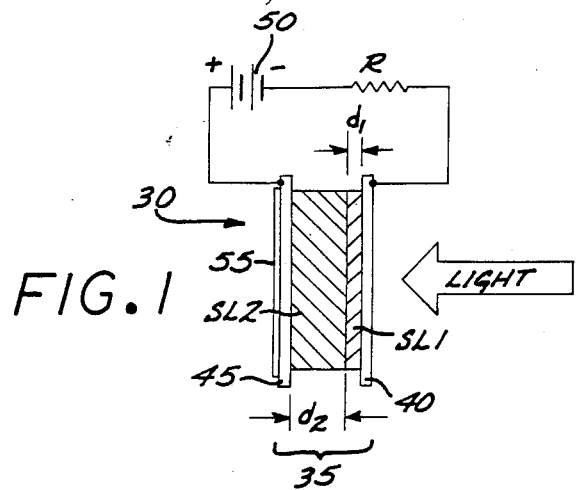
FIG. 1 is a cross-sectional diagram illustrating a preferred configuration for the fast response component of the eye protection device.

The present invention is an eye protection device employing a fast response component for blocking high intensity light and a (relatively) slow response component. As shown in FIG. 1, one preferred configuration for the fast response component 30 is a series circuit comprising a wafer including two different semiconductor layers SL1 and SL2 sandwiched between two transparent electrodes 40 and 45, a battery 50, and a resistor R. The layer SL1 has a thickness $d_1$, and the layer SL2 has a thickness $d_2$. The layer SL1 may be fabricated of a semiconductor material with a band-gap energy ($E_G$) less than that of the lowest energy visible photon at 700 nm, e.g., silicon with $E_G=1.11$ eV or 1120 nm, germanium with $E_G=0.66$ eV or 1878 nm, gallium arsenide with $E_G=1.47$ eV or 843 nm. The layer SL2 may be fabricated of a semiconductor material with a large band-gap energy, e.g., zinc sulfide with $E_G=3.58$ eV, silicon carbide with $E_G=2.8$ eV, or zinc selenide with $E_G=2.67$ eV. An exemplary material for the transparent electrodes is indium tin oxide.

Overview of the Operation of the Fast Response Component

Assume that laser light is incident on the semiconductor layer SL1 as indicated by the arrow in FIG. 1. This layer generates conducting electrons by the absorption of photons. These electrons are then injected into the intrinsic semiconductor layer SL2. The SL2 medium provides a gain mechanism which increases the number of conducting electrons. If the conducting electron density in layer SL2 results from light absorbed at intensities above the threshold for eye damage, then layer SL2 will undergo an insulator-to-metal transition. Upon becoming metal-like, layer SL2 blocks the incident light.

There are several constraints on the nature and dimensions of the layer SL1. First, the optical threshold energy (band-gap energy) of the layer SL1 must be less than that of the incident photons. Second, the recombination time of the excited electrons in the layer SL1 must be greater than the time needed to sweep these electrons into the layer SL2. Third, the thickness, $d_1$, of the layer SL1 must be small enough so that the layer SL1 is transparent below the damage threshold (which may be considered as 53 W/cm$^2$ for a $10^{-8}$ sec pulse at 500 nm, see, for example, the Proceedings of Conference on Combat Ocular Problems, Letterman Army Institute of Research, Presidio of San Francisco, 1980) yet large enough to absorb a critical number of photons above the damage threshold. Consequently, $d_1$ is approximately equal to one absorption length (optical path length where the transmitted light intensity equals $e^{-1}$ times the incident light intensity) for the semiconductor comprising layer SL1.

The voltage applied to the wafer 35 must be large enough so that the electrons in the conduction band of layer SL1 experience no significant barrier for injection into the conduction band of the layer SL2. Because the band-gap energy of SL1 ($E_G(SL1)$) is less than that of SL2 ($E_G(SL2)$), an electron in the conduction band of SL1 must overcome an energy barrier equal to $E_G(SL2)-E_G(SL1)$ if the electron is to be injected into the conduction band of SL2. Hence, the voltage applied to the wafer cannot be less than $E_G(SL2)-E_G(SL1)$, where the units are in eV.

The layer SL2 domain makes it possible to increase the number density of conducting electrons transferred to it from layer SL1, so that a critical number density of conducting electrons is obtained which results in the formation of a metallic region of skin depth $\delta < d_2$. This metallic region will then block the laser light incident on the device.

The gain across layer SL2 results from the interaction of the D.C. electric field, E, applied to the wafer and the conducting electrons in layer SL2. This interaction results in an increase of the kinetic energy of the conducting electrons so that when these electrons collide with valence electrons, more conducting electrons are produced. This effect is similar to the amplification process in an avalanche photodiode.

The constraints on the nature and dimension of layer SL2 are as follows. First, it is desirable that the band gap energy, $E_G$, of layer SL2 be greater than that of the incident photons. When this is satisfied, the incoming photons of interest do not directly create conducting electrons in the layer SL2 by radiation absorption in layer SL2. This makes it possible for the width $d_2$ of the layer SL2 to be longer than it could be if it had to be made less than an absorption length. Second, the relaxation time of the conducting electrons in the layer SL2 must be greater than both the time required to form the metallic region of skin depth $\delta < d_2$ and the laser pulse width. Third, the band gap energy $E_G$, the mobility $\mu$, and the effective mass, m, of the conducting electrons in layer SL2 must be such that an adequate gain can be obtained for reasonable values of $d_2$ and the magnitude of the electric field E applied to the wafer 35. Furthermore, the width $d_2$ should preferably be large enough so that the metallic region of skin depth, $\delta$, can form within the layer SL2, yet small enough so that the response time of the system is below 1 nsec. The value of $d_2$ can range from hundreds of Angstroms to a few microns.

A filter 55 can be placed next to the surface closest to the eye which will prevent the recombination radiation of frequency corresponding to the large band gap of layer SL2 from impinging on the eye. Typically, the dominant recombination light frequency falls in the blue light range, so the filter should be designed to attenuate light at the dominant light frequency or range while passing other visible light frequencies.

The operation of the fast response component 30 is summarized as follows:

1. Above the laser damage threshold, the light intensity generates a number of conducting electrons per unit area, N, in layer SL1.

2. The field, E, causes the conducting electrons to be transferred from layer SL1 to layer SL2.

3. The field, E, increases the kinetic energy of the conducting electrons in layer SL2 so that, when they collide with valence electrons, more conducting electrons are created.

4. If the gain across layer SL2 is G, then the number of conducting electrons per unit area in layer SL2 is GN.

5. The voltage applied to the wafer and the thickness of layer SL2 are set so that GN makes possible the formation of a metallic region of skin depth $\delta < d_2$, with layer SL2.

6. The metallic region blocks the laser light incident on the device.

7. The time constant for the formation of the metallic region is determined by the transit time of the electrons, the collision frequency, and the probability for impact ionization when the relaxation time is greater than the transit time.

8. The time constant for the existence of the metallic region or the critical number density of conducting electrons, GN, is defined by the resistance in the circuit, the capacitance of the sandwich, and the recombination time of the conducting electrons.

Theoretical Analysis

The interaction of the conducting electrons in a semiconductor with an electro-magnetic field is given by the following dispersion expression:

$$k^2 = (\omega^2/c^2)[1 - \omega_p^2/(\omega^2 + \nu^2) + i\omega_p^2(\nu/\omega)/(\omega^2 + \nu^2)] \quad (1)$$

where c is the speed of light, k is the wave vector, $\omega$ is the angular frequency of the radiation, $\omega_p$ is the plasmon frequency of the conducting electrons, and $\nu$ is the collision frequency of these electrons. If one defines $$F(\nu/\omega) = (\nu/\omega)/(1 + (\nu/\omega)^2), \quad (2)$$

then Eq. (1) becomes $$k^2 = (\omega^2/c^2)[1 - \omega_p^2][1 - \omega_p^2/(\omega^2 + \nu^2) + i(\omega_p^2/\omega^2)F(\nu/\omega)] \quad (3)$$

There are two cases where the layer SL2 behaves more like a metal than an insulator. The first case is defined by $$(\omega_p^2/\omega^2) > 1 \quad (4)$$

and $$\nu < \omega. \quad (5)$$

In this case, light will be reflected from layer SL2 because the dielectric function is negative.

The second case is defined by $$(\omega_p^2/\omega^2) < 1. \quad (6)$$

In this case, light will be attenuated by the formation of a metallic region in the layer SL2 of a skin depth given by Eq. (7)

$$\delta = 2c\omega/\omega_p F(\nu/\omega). \quad (7)$$

In order for the layer SL2 to meet the conditions of the first case, the plasmon frequency for layer SL2 must be made greater than or equal to $10^{15}$ sec$^{-1}$. The expression for the plasmon frequency is given by $$\omega_p^2 = 4\pi N e^2 G/\xi m_o d_2, \quad (8)$$

where N is the number of conducting electrons per area photo-generated in layer SL1, e is the electronic charge, G is the gain in layer SL2, $m_o$ is the electronic mass, $\xi$ is a fraction which defines the effective mass of a conducting electron in the layer SL2, and $d_2$ is the thickness of the layer SL2. For $\omega_p \geq 10^{15}$ sec$^{-1}$, and assuming a value of $N = 1.3 \times 10^{12}$ photons/cm$^2$ (the eye damage threshold at 500 nm for a $10^{-8}$ sec pulse), $$G \geq \xi d_2/\pi \times 10^{-9}. \quad (9)$$

The value of $d_2$ can range from tens of Angstroms to a few microns.

A reasonable value of $G \sim 10$ can be obtained if $\xi = 0.01$ and $d_2 = 400 \times 10^{-8}$ cm. An effective mass of $0.01 m_o$ is not an unreasonable value for semiconductors, as indicated in "Introduction to Solid State Physics," C. Kittel, at page 223, Wiley, New York, 1976.

In order for the layer SL2 to meet the conditions of the second case, the skin depth for the layer SL2 must be made less than or equal to $d_2$, or $$\delta/d_2 \leq 1. \quad (10)$$

The expanded expression for the skin depth is obtained by inserting Eq. 8 into Eq. 7.

$$\delta = 2c\omega \xi m_o d_2/4\pi N e^2 G F(\nu/\omega). \quad (11)$$

The condition on the skin depth given Eq. 10 provides the following relation:

$$2c\omega \xi m_o/4\pi N e^2 G F(\nu/\omega) < 1. \quad (12)$$

Hence, $$G > 10^4 \xi/F(\nu/\omega) \quad (13)$$

The term, $F(\nu/\omega)$, is maximized to a value of $\frac{1}{2}$ when $\nu = \omega$. Consequently, the minimum gain, $G_{min}$, is $$G_{min} > 2 \times 10^4 \xi \quad (14)$$

A reasonable value of $G_{min} \sim 2000$ can be obtained if $\xi = 0.1$. This value of $\xi$ is not unreasonable for semiconductors.

If $F(\nu/\omega)$ is to be maximized by letting $\nu = \omega$, then the mobility of conducting electrons in the layer SL2 is constrained by the expression $$\mu = 2/\xi (\text{cm}^2/\text{V-sec}). \quad (15)$$

If $\xi = 0.1$, then $\mu = 20$ cm$^2$/V-sec, a reasonable value for single-crystalline and amorphous semiconductors.

In conclusion, the theoretical analysis indicates that it is possible to achieve an insulator-to-metal transition of layer SL2 for the two cases defined by Equations 4 and 6. The gains required to induce the transition are not excessive and are consistent with the properties of known semiconductors.

Theoretical Analysis of the Current and Electric Field Distribution in the Semiconductor Layer The one-dimensional equations of continuity which define the current and electric field distribution in layer SL2 are $$\partial n_e/\partial t = \partial J_e/\partial x + \nu P_1 n_e, \quad (16)$$

$$\partial n_H/\partial t = \nu P_1 n_e, \quad (17)$$

$$\partial E/\partial x = 4\pi e(n_H - n_e), \quad (18)$$

$$J_e = -\mu E n_e, \quad (19)$$

where $n_e$ is the number density of conducting electrons, $n_H$ is the number density of holes, E is the electric field, $J_e$ is the current density of the conducting electrons, $\nu$ is the collision frequency of electrons, $P_1$ is the probability of conducting electron pair production as a result of collision, $\mu$ is the mobility of the conducting electrons, e is the electronic charge, x is the distance from the layer SL1–SL2 interface, and t is time. The contribution of electron diffusion to $J_e$ in Equation 19 has been neglected because it is small. Also, the electrons are assumed to be much more mobile than the holes and so the contribution of the holes to the current is neglected.

The subtraction of Equation 17 from Equation 16 and the insertion of Equation 19 into Equation 16 yields $$\partial(n_e - n_H)/\partial t = \partial(\mu E n_e)/\partial x. \quad (20)$$

The insertion of the expression for $(n_e - n_H)$ in Equation 18 into Equation 20 provides $$\partial^2 E/\partial t \partial x = 4\pi e \partial(\mu E n_e)/\partial x. \quad (21)$$

Equation 21 then implies that $$\partial E/\partial t + 4\pi e \mu E n_e = J(t), \quad (22)$$

where J(t) is the time-dependent current. It is found that $$\partial E/\partial t << 4\pi e \mu E n_e, \quad (23)$$

i.e., the displacement current is small compared to the conduction current. Thus, $$E = J/4\pi e \mu n_e \quad (24)$$

Furthermore, Equation 24 shows that the electric field is not dependent on x in the lowest approximation.

If Equation 19 is inserted into Equation 16 and with E not dependent on x, then $$\partial n_e/\partial t = \nu P_1 n_e. \quad (25)$$

The expression for $P_1$ is given by $$P_1 = exp(-E_1/2m\mu^2 E^2), \quad (26)$$

where $E_1$ is the minimum energy to produce two conducting electrons by a collision and m is the effective mass of the conducting electrons. The energy $E_1$ is usually taken to be 1½–2 times the band gap energy of the semiconductor. The insertion of Equation 24 into Equation 26 yields $$(1/n_e)\partial n_e/\partial t = \nu exp(-E_1(4\pi e)^2 n_e^2/2mj^2), \quad (27)$$

If $$\beta = E_1(4\pi e)^2 n_e^2/2mJ^2, \quad (28)$$

then $$(exp(\beta)/\beta)d\beta = 2\nu t. \quad (29)$$

The exact solution of Equation 28 is $$E_i(\beta) = 2\nu t + C' \quad (30)$$

where $E_i(\beta)$ is the exponential integral, and C' is a constant. The assmyptotic solution to Equation 29 is sufficient here, and it is $$(1.0C)exp(\beta)/\beta = 2\nu t_p, \quad (31)$$

where $t_p$ is the pulse width of the laser pulse.

If $\nu = 10^{13}$ sec$^{-1}$ and $t_p = 10^{-8}$ sec, and Equation 31 is solved for $\beta$, then $\beta \simeq 15$. If $\nu = 10^{15}$ sec$^{-1}$ had been used, the $\beta \simeq 20$. Now, $$J = N/t_p, \quad (32)$$

$$m = \xi m_o, \quad (33)$$

$$E_1 = \eta \times 10^{-12}, \quad (34)$$

where N is the number of conducting electrons per unit area photo-generated in the first semiconductor layer ($1.3 \times 10^{12}$ photons/cm$^2$ at the damage threshold for a $10^{-8}$ sec pulse at 500 nm), $\xi$ is a constant, $m_o$ is the electronic mass, and $\nu$ is a constant. Inserting Equations 32–34 into Equation 28 and using $\beta \simeq 15$, yields $$n_e \sim (\xi/\eta) 4.4 \times 10^{22} cm^{-3}, \quad (35)$$

This number density is very high and indicates clearly that an insulator-to-metal transition is possible within the semiconductor. Most semiconductors will undergo an insulator-to-metal transition at number densities less than that give in Equation 35 (i.e., $10^{19} - 10^{20}$ cm$^{-3}$).

Thus, the system should become opaque well before the end of the 10 nanosecond pulse. The associated fields are large ($\leq 10^5$ V/cm) but less than zener-breakdown fields.

In conclusion, the theoretical analysis indicates that the current density and electric field within the semiconductor layer are independent of time and position. Namely, high number densities of conducting electrons can be generated in the semiconductor which then induce the insulator-to-metal transition.

A configuration for the fast response component of a protective device against visible pulsed laser light was described above. The component includes a wafer comprising two different semiconductor layers sandwiched between two transparent electrodes. The function of the first layer is to generate conducting electrons by the absorption of photons. These electrons are then injected into the second layer. This layer provides a gain mechanism which increases the number of conducting electrons. If the number density in the second layer results from light absorbed at intensities above the threshold for eye damage, then this layer will undergo an insulator-to-metal transition. Upon becoming metal-like, the second layer then blocks the incident light.

In conclusion, the fast response component appears to meet the major requirements for a protective device against pulsed laser light in the visible region with very short pulse widths. These requirements are fast response within a few picoseconds to nanoseconds, and broadband wavelength protection.

In order to protect against laser pulses of a microsecond or longer, a slow response component comprising a PLZT (lanthanum-modified lead zirconium titanate) or similar electro-optic shutter may be used in combination with the fast response component. Depending on the particular application requirements, such a slow response component may be unnecessary.

The Preferred Embodiment of a Protective Device

Figure 2:
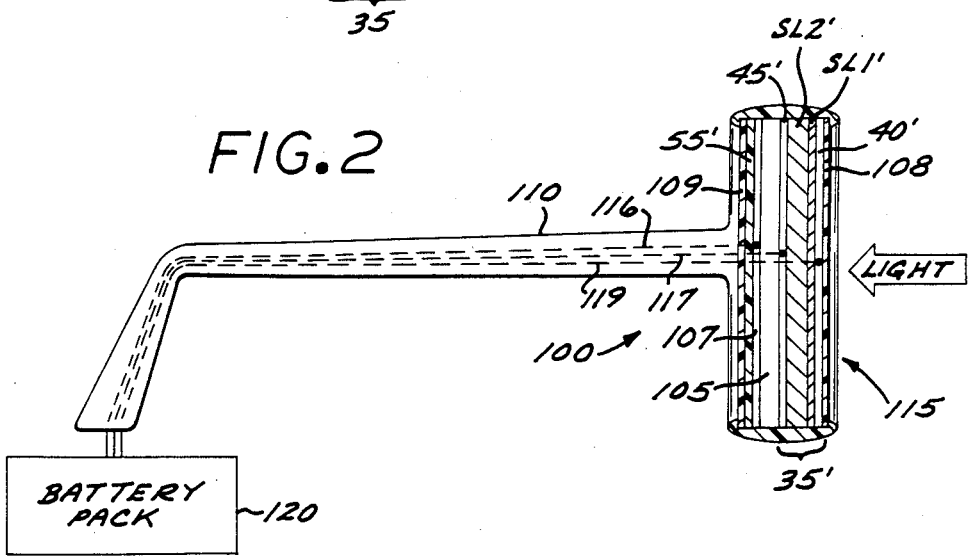
FIG. 2 is a side cross-sectional view of an eye protection device embodying the invention.
Figure 3:
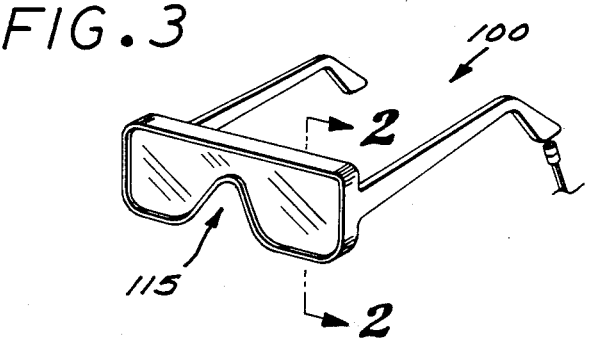
FIG. 3 is a perspective view of the eye protection device of FIG. 2.
Figure 4:
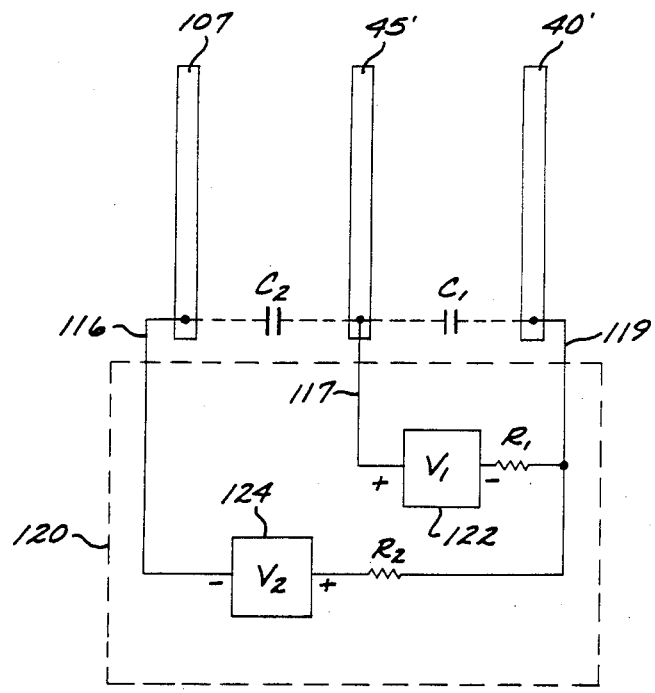
FIG. 4 is an electrical schematic illustrating the effective electrical circuit of the embodiment of FIG. 2.

Referring now to FIGS. 2–4, a protective eye goggle embodying the invention is disclosed. The goggle comprises the goggle portion 115 which is secured in position in front of the wearer's eye by the temple and ear pieces 110. The goggle frame and the temple and ear pieces are preferably fabricated from a suitable plastic material, such as polycarbonate, so as to provide ballistic and chemical protection. The goggle portion comprises the fast response component 35' and the (relatively) slow response component 105. The fast response component 35' is similar to the component 35 shown in FIG. 1, comprising the respective transparent electrodes 40' and 45', the wafer comprising two adjacent layers SL1' and SL2' of different semiconductor materials, and the battery pack 120 connected to the fast and slow response components by wire leads 116, 117 and 119. A third transparent electrode 107 is formed on the surface of the slow response component 105 adjacent the user's eye. The battery lead 116 is connected to electrode 107, battery lead 117 to electrode 45', and lead 119 to electrode 40'.

In this embodiment, the electrodes 40', 45' and 107 are fabricated from indium tin oxide. The semiconductor layer SL1' is a layer of silicon having a thickness of about 600 Angstroms. The semiconductor layer SL2' is a layer of zinc sulfide having a thickness of about 2μm.

The slow response component 105 preferably comprises a PLZT electro-optic shutter. This is an active device powered by a battery. Such shutters are known in the art, as described, for example, in "PLZT Electro Optic Shutters: Applications," J. T. Cutchan et al., Appl. Opt. 14 (1975), the entire contents of which are incorporated herein by this reference. PLZT electro-optic shutters are commercially available, e.g., from the Communication Systems Division of Motorola, Inc., Albuquerque, N.M.

The fast response component 35' may be fabricated through a sequence of thin-film depositions. A preferred deposition technique is photo-chemical vapor deposition because it can deposit thin-films at lower temperatures than the standard RF-magnetron sputtering technique. The sequence of depositions is as follows:

(1) Deposition of first indium-tin-oxide (ITO) transparent electrode 45'.

An ITO transparent electrode (thickness of approximately 1500 Angstroms) is deposited onto the light receiving surface of the PLZT electro-optic shutter.

(2) Deposition of zinc sulfide (ZnS) wide band-gap semiconductor layer (SL2').

An amorphous ZnS film (thickness on the order of micrometers) is deposited on top of the ITO transparent electrode 45'.

(3) Deposition of silicon (Si) narrow band-gap semiconductor layer (SL1').

An amorphous Si thin-film (thickness of approximately 600 Angstroms) is deposited on top of the ZnS film.

(4) Deposition of second ITO transparent electrode 40'.

An ITO transparent electrode similar to the electrode 45' is deposited onto the Si thin-film. A transparent electrode 107 is deposited on the surface of the PLZT electro-optic shutter from which light exits in a similar manner as described above for layers 40' and 45'. Electrical contact of the ITO electrodes 107, 40' and 45' may be established using conductive silver epoxy. Wires 116, 117 and 119 lead from these contact points to the battery pack 120. A filter 55' 30 which attenuates recombination radiation emitted from the SL2' layer may be laminated as shown to the transparent electrode 107 if desired for a particular application. Transparent polycarbonate plates 108 and 109 are preferably placed over the composite structure of the fast and slow response components in order to prevent them from being scratched.

The effective electrical circuit of the embodiment of FIGS. 2 and 3 is shown in FIG. 4. The battery pack 120 comprises two batteries 122 and 124. In this embodiment, the voltage $V_1$ of the first battery 122 is 160 volts, and the voltage $V_2$ of the second battery 124 is 200 volts. The batteries 122 and 124 have respective series resistors $R_1$ and $R_2$ associated therewith, which represents either a discrete resistance or the internal battery resistance. Two series circuits are made to connect to the electrodes 40', 45' and 107.

The first circuit powers the fast response component 35', with the positive terminal of the battery 122 connected to electrode 45' via lead 117, and the negative terminal of the battery 122 connected to electrode 40' through resistor $R_1$ via lead 119. The capacitance $C_1$ (shown in phantom) represents the capacitance of the sandwich structure of the fast response component 35' when it is in the transparent state.

The second circuit powers the slow response component 105. The battery 124 is connected in reverse polarity to the connection of the battery 122. Thus, the negative terminal of the battery 124 is connected to the electrode 107 via lead 116, and the positive terminal of the battery 124 is connected through resistor $R_2$ via lead 119 to the electrode 40'. The capacitance $C_2$ (shown in phantom) represents the capacitance of the slow response component when it is in the transparent state.

The electrical circuits may also include on/off switches (not shown) for disconnecting the power to the device 100.

The device 100 operates in the following manner. When the incident light intensity is below the eye damage threshold, no current flows through either the first or second circuits. A battery voltage of 160 volts is applied across the fast response component. Because of the reverse polarity connections of the two batteries 122 and 124, the voltage of the battery 122 bucks that of the battery 124, so that only a net voltage of 40 volts is applied across the slow response component 105 between the electrodes 45' and 107. In this embodiment, an applied voltage of 40 volts is insufficient to trigger the component 107 from the transparent state to the opaque state. Thus, both components are in the transparent state.

Once the incident light intensity exceeds the eye damage threshold, the fast response component becomes conductive and turns opaque, discharging the capacitance $C_1$. The voltage drop is now across the resistor $R_1$ instead of the fast response component 35'. With the voltage $V_1$ of the battery 122 no longer bucking that of the battery 124, the full voltage $V_2$ of the battery 124 is now applied across the slow response component 105. An applied voltage of 200 volts is sufficient to trigger the slow response component 105, causing it to become opaque.

When the incident light intensity falls below the eye damage threshold, the fast response component becomes transparent and nonconductive, thereby once again reducing the applied voltage across the slow response component to 40 volts. This causes the component 105 to change states back to the transparent state.

It is understood that the above-described embodiments are merely illustrative of the possible specific embodiments which may incorporate principles of the present invention. Other arrangements may readily be devised in accordance with these principles by those skilled in the art without departing from the scope of the invention.

What is claimed is:

1. An eye protection device against broadband high intensity light, which includes a fast response protection component, comprising:
   an assembly comprising first and second transparent electrode members, sandwiching first and second semiconductor layers;
   said first layer comprising a layer of a first semiconductor material having a characteristic threshold energy less than that of incident high intensity light, and wherein the recombination time of excited electrons in the first layer is greater than the time needed to sweep these electrons into the second layer, and wherein the thickness of the first layer is approximately equal to one absorption length for said first semiconductor material; and
   wherein said second layer comprises a semiconductor material having a characteristic threshold energy greater than that of incident high intensity light, and wherein the width of the second layer is large enough so that a metal region of a skin depth can form in the second layer; and
   a filter disposed on a surface of one of said transparent electrodes adjacent the eye for attenuating light at a frequency of the recombination radiation corresponding to the characteristic band gap energy of the second layer semiconductor material; and
   means for developing a sufficient electric field across the first and second layers such that electrons in the conduction band of the first layer experience no significant barrier for injection into the conduction band of the second layer.

2. The eye protection device of claim 1 wherein said fast response component is embedded in a plastic material to provide ballistic and chemical protection.

3. The eye protection device of claim 1 wherein said width of said second semiconductor layer is in the range of tens of Angstroms to a few microns.

4. The eye protection device of claim 1 wherein said first semiconductor material is silicon, and said second semiconductor material is zinc sulfide.

5. The eye protection device of claim 1 wherein said means for developing an electric field comprises a battery for applying a potential difference between said first and second electrodes.

6. The eye protection device of claim 1 wherein said first and second electrodes comprise substantially planar layers comprising indium tin oxide.

7. An eye protection device against broadband high intensity light, comprising:
   a first transparent electrode having a surface extending over the viewing area of said device;
   a second transparent electrode having a surface extending over said viewing area and disposed in a substantially parallel aligned relationship with said first electrode;
   first and second adjacent semiconductor layers disposed between said first and second electrodes, said first layer comprising silicon having a depth of approximately 600 Angstroms and said second layer comprising zinc sulfide having a depth in the range of hundreds of Angstroms to tens of micrometers;
   said first and second electrodes and said first and second semiconductor layers being substantially planar;
   means for applying an electric field transverse to said layers;
   said first layer transparent to incident high intensity light and comprising a means for generating conducting electrons by the absorption of photons, the resulting electrons being injected into said second layer by said electric field;
   said first layer being transparent to incident light intensities below a predetermined intensity and comprising means for increasing the number of conducting electrons injected from the first layer due to the interaction of said electric field and said conducting electrons, whereby for incident light intensities above said threshold, sufficient conducting electrons are formed in said second layer to cause an insulator-to-metal transition of material comprising said second layer, said layer becoming opaque and thereby blocking said incident high intensity light.

8. The protection device of claim 7, wherein said first layer has a first predetermined depth approximately equal to one absorption length for said first semiconductor material.

9. The protection device of claim 7 wherein said second semiconductor material has a characteristic band gap energy which is greater than that of incident high intensity light and wherein the second layer has a second depth which is greater than an absorption length in said second semiconductor material.

10. The protective device of claim 7 wherein said device provides protection against pulsed laser light radiation, and wherein the relaxation time of conducting electrons in said second layer is greater than the laser pulse with and the time required to form said insulation-to-metallic transition.

11. An eye protection device against broadband high intensity light, comprising:
   (a) a fast response protection component, comprising first and second semiconductor layers, said first layer comprising a layer of a first semiconductor material having a characteristic threshold energy less than that of incident high intensity light, and wherein the recombination time of excited electrons in the first layer is greater than the time needed to sweep these electrons into the second layer, and wherein the thickness of the first layer is small enough so that the first layer is transparent for incident light intensities below the eye damage threshold and yet is large enough to absorb a critical number of photons of incident light at a level of intensity above the damage threshold, and wherein said second layer comprises a semiconductor material having a characteristic band gap energy greater than that of incident high intensity light, and wherein the width of the second layer is large enough so that a metal region of a predetermined skin depth can form in the second layer, and further comprising a means for developing a sufficient electric field across the first and second layers such that electrons in the conduction band experience no significant barrier for injection into the conduction band of the second layer; and (b) a slow response protection component which is transparent to light of intensities below the eye damage threshold, and which relatively slowly becomes opaque to incident high intensity light.

12. The eye protection device of claim 11 wherein said slow component device comprises an electro-optic shutter.

13. The eye protection device of claim 12 wherein said electro-optic shutter comprises a lanthanum-modified lead zirconium titanate shutter.

14. The eye protection device of claim 11 further comprising a filter for attenuating light at a frequency of the recombination radiation corresponding to the characteristic band gap energy of the second layer semiconductor material.

15. The eye protection device of claim 11 wherein said first and second components are embedded in a plastic material to provide ballistic and chemical protection.

16. The eye protection device of claim 11 wherein said width of said first semiconductor layer is approximately equal to one absorption length for said first semiconductor material.

17. The eye protection device of claim 11 wherein said width of said second semiconductor layer is in the range of hundreds of Angstroms to a few microns.

18. The eye protection device of claim 11 wherein said first semiconductor material is silicon, and said second semiconductor material is zinc sulfide.

19. The eye protection device of claim 11 wherein said means for developing an electric field comprises first and second transparent electrode members sandwiching said fast response protection component and said slow response protection component, and a battery pack for applying a potential difference between said first and second electrodes.

20. The eye protection device of claim 19 wherein said first and second electrodes comprise substantially planar layers comprising indium tin oxide.

21. The eye protection device of claim 11 wherein:
(i) said slow response component comprises an electro-optic shutter activated by application of an electrical potential difference exceeding a first predetermined threshold;
(ii) said means for developing said sufficient potential difference across said first and second layers comprises first and second transparent electrode members sandwiching said fast response component, and first voltage source means for applying a first voltage across said first and second electrode members; and
(iii) means for applying said potential difference to said electro-optic shutter to activate said shutter to operate in an opaque state.

22. The eye protection device of claim 20 further comprising a third transparent electrode member disposed so that said first electrode member and said third electrode member sandwich said fast response component and said slow response component, and wherein:
said means for applying said potential difference to said electro-optic shutter comprises a second voltage supply source for applying a second voltage across said first and third electrode;
said first voltage source means comprises a series resistance;
said second voltage source means is connected in the opposite polarity sense to that of said first voltage source; and
the magnitudes of the voltages developed by said respective first and second voltage sources are cooperatively selected such that, when light intensities below the eye damage threshold are incident on said device, said fast response component is transparent and substantially no current flows through said resistance, so that the net potential difference across said slow response component is effectively the difference between the voltage magnitudes of the second and first voltage sources, that difference being insufficient to activate the slow response component to operate in an opaque state, and when the incident light intensity exceeds the eye damage threshold, the fast response component becomes opaque, and substantially the full voltage produced by said second voltage source is across said slow response component, causing said slow response component to operate in the opaque state.

* * * * *